(12) United States Patent
Yu (10) Patent No.: US 11,771,331 B2
(45) Date of Patent: Oct. 3, 2023

(54) ELECTRONIC SPHYGMOMANOMETER MEASURING METHOD, SYSTEM, ELECTRONIC SPHYGMOMANOMETER, AND STORAGE MEDIUM

(71) Applicant: GUANGDONG TRANSTEK MEDICAL ELECTRONICS CO., LTD., Zhongshan (CN)

(72) Inventor: Wenhan Yu, Zhongshan (CN)

(73) Assignee: GUANGDONG TRANSTEK MEDICAL ELECTRONICS CO., LTD., Zhongshan (CN)

( * ) Notice: Subject to any disclaimer, the term of this patent is extended or adjusted under 35 U.S.C. 154(b) by 517 days.

(21) Appl. No.: 16/976,476

(22) PCT Filed: May 29, 2018

(86) PCT No.: PCT/CN2018/088786
§ 371 (c)(1),
(2) Date: Aug. 28, 2020

(87) PCT Pub. No.: WO2019/165717
PCT Pub. Date: Sep. 6, 2019

(65) Prior Publication Data
US 2021/0000354 A1    Jan. 7, 2021

(30) Foreign Application Priority Data

Feb. 28, 2018   (CN) .......................... 201810167529.0

(51) Int. Cl.
*A61B 5/022* (2006.01)
*A61B 5/00* (2006.01)
(Continued)

(52) U.S. Cl.
CPC ........ *A61B 5/02225* (2013.01); *A61B 5/0225* (2013.01); *A61B 5/7278* (2013.01);
(Continued)

(58) Field of Classification Search
CPC ..... A16B 5/022; A16B 5/02225; A16B 5/021; A16B 5/7203; A16B 17/1355; A16B 17/135

See application file for complete search history.

(56) References Cited

U.S. PATENT DOCUMENTS

| | | |
|---|---|---|
| 4,984,577 A | 1/1991 | Frankenreiter |
| 2011/0021927 A1 | 1/2011 | Sawanoi et al. |

(Continued)

FOREIGN PATENT DOCUMENTS

| | | |
|---|---|---|
| CN | 1394546 | 2/2003 |
| CN | 1698535 | 11/2005 |

(Continued)

OTHER PUBLICATIONS

Search Report for International Patent Application PCT/CN2018/088786, dated Sep. 6, 2019.

(Continued)

*Primary Examiner* — Kaylee R Wilson
*Assistant Examiner* — Martin Nathan Ortega
(74) *Attorney, Agent, or Firm* — FRESH IP PLC; Clifford D. Hyra; Aubrey Y. Chen (57) ABSTRACT

An electronic sphygmomanometer measuring method, comprising: acquiring a barometric pressure sequence (S110); obtaining a systolic pressure/diastolic pressure on the basis of the barometric pressure sequence (S120); extracting characteristic information of the barometric pressure sequence (S130); and correcting the systolic pressure/diastolic pressure on the basis of the characteristic information (S140). The measuring method increases the precision in calculating the systolic pressure/diastolic pressure. Also disclosed accordingly are an electronic sphygmomanometric system, an electronic sphygmomanometer, and a storage medium.

15 Claims, 5 Drawing Sheets

(51) Int. Cl.
*A61B 5/0225* (2006.01)
*A61B 5/021* (2006.01)

(52) U.S. Cl.
CPC ............... *A61B 5/00* (2013.01); *A61B 5/021* (2013.01); *A61B 5/02116* (2013.01); *A61B 5/7203* (2013.01)

(56) References Cited

U.S. PATENT DOCUMENTS

| | | | |
|---|---|---|---|
| 2011/0054331 A1 | 3/2011 | Shih et al. | |
| 2015/0201851 A1 | 7/2015 | Kubo | |
| 2016/0360981 A1* | 12/2016 | Kang | A61B 5/681 |

FOREIGN PATENT DOCUMENTS

| | | | | |
|---|---|---|---|---|
| CN | 1868399 | 11/2006 | | |
| CN | 101340845 | 1/2009 | | |
| CN | 102202567 | 9/2011 | | |
| CN | 102283638 | 12/2011 | | |
| CN | 104367308 | 2/2015 | | |
| CN | 105615845 | 6/2016 | | |
| CN | 106510669 | 3/2017 | | |
| CN | 107174230 | 9/2017 | | |
| CN | 107320088 | 11/2017 | | |
| CN | 107320089 | 11/2017 | | |
| JP | H05-309073 A | * | 8/1993 | ............. A16B 5/022 |
| WO | 2016/030232 A1 | | 3/2016 | |

OTHER PUBLICATIONS

Office Action for Priority Application 201810167529.0.
Written Opinion for International Application No. PCT/CN2018/088786.
Search Report for EP application No. 18907855.3-1113/3760110, dated Apr. 13, 2021.
Office Action for EP application No. 18907855.3-1113, dated Apr. 16, 2021.

* cited by examiner

ELECTRONIC SPHYGMOMANOMETER MEASURING METHOD, SYSTEM, ELECTRONIC SPHYGMOMANOMETER, AND STORAGE MEDIUM

CROSS-REFERENCE TO RELATED APPLICATIONS

The present disclosure claims priority to Chinese Patent Application No. 2018101675290, filed with the Chinese Patent Office on Feb. 28, 2018, entitled "Measuring Method and System for Electronic Sphygmomanometer, and Electronic Sphygmomanometer", which is incorporated herein by reference in its entirety.

TECHNICAL FIELD

The present disclosure relates to the technical field of measurement with electronic sphygmomanometers, and in particular to a measuring method and system for an electronic sphygmomanometer, an electronic sphygmomanometer, and a storage medium.

BACKGROUND ART

Electronic sphygmomanometers using the principle of oscillometry have been commercially available for many years. This type of electronic sphygmomanometer has an air bag (or a cuff) wrapped around a certain part of a human body. The air bag may be inflated/deflated by controlling the elements such as an air pump and an air valve, so that the amount of air in the air bag is changed, and then air pressure values are collected. Here, the process of inflation/deflation of the air bag is basically performed by using two schemes in the prior art. One scheme involves rapid inflation followed by gentle deflation, wherein the air pressure pulsation information is collected during the gentle deflation. The other scheme involves gentle inflation followed by rapid deflation, wherein the air pressure pulsation information is collected during the gentle inflation.

In either the inflation-based measurement mode or the deflation-based measurement mode, an envelope curve thereof is generated with an abscissa (basic air pressure) descending in order from left to right. Identical envelope curves are generated in the above two measurement modes, and the envelope curves are calculated from air pressure values to obtain systolic/diastolic blood pressure of a subject in both of the measurement modes. However, the systolic/diastolic blood pressure calculated in the two measurement modes is calculated using only one parameter which is the envelope curve. The use of a single parameter leads to insufficiently accurate blood pressure calculations.

SUMMARY

In view of this, an object of the present disclosure is to provide a measuring method and system for an electronic sphygmomanometer, an electronic sphygmomanometer, and a storage medium, which can increase the accuracy in the calculation of systolic/diastolic blood pressure by calculating the systolic/diastolic blood pressure from a sequence of air pressure values, extracting characteristic information from a sequence of air pressure pulsations, and correcting the systolic/diastolic blood pressure on the basis of the characteristic information.

In a first aspect, the present disclosure provides a measuring method for an electronic sphygmomanometer, comprising: acquiring a sequence of air pressure values; obtaining systolic/diastolic blood pressure on the basis of the sequence of air pressure values; extracting characteristic information from the sequence of air pressure values; and correcting the systolic/diastolic blood pressure on the basis of the characteristic information.

With reference to the first aspect, the present disclosure provides a first possible embodiment of the first aspect, wherein the extracting characteristic information from the sequence of air pressure values comprises: separately extracting a sequence of air pressure pulsations and a sequence of basic air pressure values from the sequence of air pressure values; calculating first derivatives of the sequence of air pressure pulsations, and selecting a minimum value from the first derivatives of the sequence of air pressure pulsations; and acquiring a basic air pressure value corresponding to an air pressure pulsation corresponding to the minimum value, so as to correct the systolic/diastolic blood pressure by using the minimum value and the basic air pressure value corresponding to the minimum value as characteristic information.

With reference to the first aspect, the present disclosure provides a second possible embodiment of the first aspect, wherein the correcting the systolic/diastolic blood pressure on the basis of the characteristic information comprises: correcting the systolic blood pressure according to equation (1), $$Sys = A + B^*Sys0 + C^*Dp\text{min} + D^*Pdp\text{min} \quad (1)$$

where Sys is the corrected systolic blood pressure, Sys0 is the systolic blood pressure to be corrected, Dpmin is the minimum value of the first derivatives of the air pressure pulsations, Pdpmin is the basic air pressure value corresponding to the minimum value, A, B, C, and D are all coefficients, A is in unit of mmHg, C is in unit of s, and B and D are dimensionless;

correcting the diastolic blood pressure according to equation (2), $$Dia = E + F^*Dia0 + G^*Dp\text{min} + H^*Pdp\text{min} \quad (2)$$

where Dia is the corrected diastolic blood pressure, Dia0 is the diastolic blood pressure to be corrected, E, F, G, and H are all coefficients, E is in unit of mmHg, G is in unit of s, and F and H are dimensionless.

With reference to the first aspect, the present disclosure provides a third possible embodiment of the first aspect, which further comprises: calculating the values of the coefficients A, B, C, and D in Equation (1) on the basis of systolic blood pressure reference values obtained from multiple clinical data and on the basis of the multiple clinical data; and calculating the values of the coefficients E, F, G, and H in Equation (2) on the basis of diastolic blood pressure reference values obtained from multiple clinical data and on the basis of the multiple clinical data.

With reference to the first aspect, the present disclosure provides a fourth possible embodiment of the first aspect, wherein the calculating the values of the coefficients A, B, C, and D in Equation (1) on the basis of systolic blood pressure reference values obtained from multiple clinical data and on the basis of the multiple clinical data comprises: acquiring systolic blood pressure reference values from multiple clinical data to form a column vector Y1 of the systolic blood pressure reference values; forming a column vector x1 on the basis of the number of the clinical data; obtaining systolic blood pressure corresponding to each clinical data on the basis of the multiple clinical data to form a column vector x2; obtaining a minimum value of first derivatives of a sequence of air pressure pulsations corresponding to each clinical data on the basis of the multiple clinical data to form a column vector x3; obtaining a basic air pressure value corresponding to the minimum value on the basis of the minimum value of the first derivatives of the sequence of air pressure pulsations corresponding to each clinical data to form a column vector x4; and obtaining the coefficients A, B, C, and D in Equation (1) on the basis of the column vector x1, the column vector x2, the column vector x3, the column vector x4, and the column vector Y1.

With reference to the first aspect, the present disclosure provides a fifth possible embodiment of the first aspect, wherein the calculating the values of the coefficients E, F, G, and H in Equation (2) on the basis of diastolic blood pressure reference values obtained from multiple clinical data and on the basis of the multiple clinical data comprises: acquiring diastolic blood pressure reference values from multiple clinical data to form a column vector Y2 of the diastolic blood pressure reference values; forming a column vector x5 on the basis of the number of the clinical data; obtaining diastolic blood pressure corresponding to each clinical data on the basis of the multiple clinical data to form a column vector x6; obtaining a minimum value of first derivatives of a sequence of air pressure pulsations corresponding to each clinical data on the basis of the multiple clinical data to form a column vector x7; obtaining a basic air pressure value corresponding to the minimum value on the basis of the minimum value of the first derivatives of the sequence of air pressure pulsations corresponding to each clinical data to form a column vector x8; and obtaining the coefficients E, F, G, and H in Equation (2) on the basis of the column vector x5, the column vector x6, the column vector x7, the column vector x8, and the column vector Y2.

With reference to the first possible embodiment of the first aspect, the present disclosure provides a sixth possible embodiment of the first aspect, wherein the separately extracting a sequence of air pressure pulsations and a sequence of basic air pressure values from the sequence of air pressure values includes: separately extracting a sequence of air pressure pulsations and a sequence of basic air pressure values from the sequence of air pressure values by a high-pass filtering algorithm, a band-pass filtering algorithm, or a moving average filtering algorithm.

With reference to the first possible embodiment of the first aspect, the present disclosure provides a seventh possible embodiment of the first aspect, wherein the calculating the first derivatives of the sequence of air pressure pulsations comprises: calculating a difference between the current air pressure pulsation value and the previously measured air pressure pulsation value; dividing the difference by a preset sampling period to obtain the first derivative of the current air pressure pulsation value; and determining the first derivatives of the sequence of air pressure pulsations based on the first derivatives of the respectively measured air pressure pulsation values.

In a second aspect, the present disclosure further discloses a measuring system for an electronic sphygmomanometer, comprising: an acquisition module, configured to acquire a sequence of air pressure values; a calculation module, coupled to the acquisition module and configured to obtain systolic/diastolic blood pressure on the basis of the sequence of air pressure values; an extraction module, coupled to the acquisition module and configured to extract characteristic information from the sequence of air pressure values; and a correction module, coupled to the calculation module and to the extraction module, respectively, and configured to correct the systolic/diastolic blood pressure on the basis of the characteristic information.

With reference to the second aspect, the present disclosure provides a first possible embodiment of the second aspect, wherein the extraction module comprises: a sequence extraction submodule, configured to separately extract a sequence of air pressure pulsations and a sequence of basic air pressure values from the sequence of air pressure values; a derivative calculation submodule, configured to calculate first derivatives of the sequence of air pressure pulsations and select a minimum value from the first derivatives of the sequence of air pressure pulsations; and an air pressure value acquisition submodule, configured to acquire a basic air pressure value corresponding to an air pressure pulsation corresponding to the minimum value, so as to correct the systolic/diastolic blood pressure by using the minimum value and the basic air pressure value corresponding to the minimum value as characteristic information.

With reference to the second aspect, the present disclosure provides a second possible embodiment of the second aspect, wherein the correction module comprises: a systolic blood pressure correcting submodule, configured to correct the systolic blood pressure according to equation (1), $$Sys = A + B * Sys0 + C * Dp\text{min} + D * Pdp\text{min} \quad (1)$$

where Sys is the corrected systolic blood pressure, Sys0 is the systolic blood pressure to be corrected, Dpmin is the minimum value of the first derivatives of the air pressure pulsations, Pdpmin is the basic air pressure value corresponding to the minimum value, A, B, C, and D are coefficients, A is in unit of mmHg, C is in unit of s, and B and D are dimensionless; and a diastolic blood pressure correcting submodule, configured to correct the diastolic blood pressure according to equation (2), $$Dia = E + F * Dia0 + G * Dp\text{min} + H * Pdp\text{min} \quad (2)$$

where Dia is the corrected diastolic blood pressure, Dia0 is the diastolic blood pressure to be corrected, E, F, G, and H are all coefficients, E is in unit of mmHg, G is in unit of s, and F and H are dimensionless.

With reference to the second possible embodiment of the second aspect, the present disclosure provides a third possible embodiment of the second aspect, which further comprises: a first calculation module, configured to calculate the values of the coefficients A, B, C, and D in Equation (1) on the basis of systolic blood pressure reference values obtained from multiple clinical data and on the basis of the multiple clinical data; and a second calculation module, configured to calculate the values of the coefficients E, F, G, and H in Equation (2) on the basis of diastolic blood pressure reference values obtained from multiple clinical data and on the basis of the multiple clinical data.

With reference to the third possible embodiment of the second aspect, the present disclosure provides a fourth possible embodiment of the second aspect, wherein the first calculation module is configured to: acquire systolic blood pressure reference values from multiple clinical data to form a column vector Y1 of the systolic blood pressure reference values; form a column vector x1 on the basis of the number of the clinical data; obtain systolic blood pressure corresponding to each clinical data on the basis of the multiple clinical data to form a column vector x2; obtain a minimum value of first derivatives of a sequence of air pressure pulsations corresponding to each clinical data on the basis of the multiple clinical data to form a column vector x3; obtain a basic air pressure value corresponding to the minimum value on the basis of the minimum value of the first derivatives of the sequence of air pressure pulsations corresponding to each clinical data to form a column vector x4; and obtain the coefficients A, B, C, and D in Equation (1) on the basis of the column vector x1, the column vector x2, the column vector x3, the column vector x4, and the column vector Y1.

With reference to the third possible embodiment of the second aspect, the present disclosure provides a fifth possible embodiment of the second aspect, wherein the second calculation module is configured to: acquire diastolic blood pressure reference values from multiple clinical data to form a column vector Y2 of the diastolic blood pressure reference values; form a column vector x5 on the basis of the number of the clinical data; obtain diastolic blood pressure corresponding to each clinical data on the basis of the multiple clinical data to form a column vector x6; obtain a minimum value of first derivatives of a sequence of air pressure pulsations corresponding to each clinical data on the basis of the multiple clinical data to form a column vector x7; obtain a basic air pressure value corresponding to the minimum value on the basis of the minimum value of the first derivatives of the sequence of air pressure pulsations corresponding to each clinical data to form a column vector x8; and obtain the coefficients E, F, G, and H in Equation (2) on the basis of the column vector x5, the column vector x6, the column vector x7, the column vector x8, and the column vector Y2.

With reference to the first possible embodiment of the second aspect, the present disclosure provides a sixth possible embodiment of the second aspect, wherein the sequence extraction submodule is configured to: separately extract a sequence of air pressure pulsations and a sequence of basic air pressure values from the sequence of air pressure values by a high-pass filtering algorithm, a band-pass filtering algorithm, or a moving average filtering algorithm.

With reference to the first possible embodiment of the second aspect, the present disclosure provides a seventh possible embodiment of the second aspect, wherein the derivative calculation submodule is configured to: calculate a difference between the current air pressure pulsation value and the previously measured air pressure pulsation value; divide the difference by a preset sampling period to obtain the first derivative of the current air pressure pulsation value; and determine the first derivatives of the sequence of air pressure pulsations based on the first derivatives of the respectively measured air pressure pulsation values.

In a third aspect, the present disclosure further provides an electronic sphygmomanometer, comprising: a collecting component and the measuring system for an electronic sphygmomanometer described in any one of the above embodiments; wherein the collecting component is configured to collect air pressure values.

The present disclosure brings about the following beneficial effects: systolic/diastolic blood pressure can be calculated with increased accuracy by calculating the systolic/diastolic blood pressure from a sequence of air pressure values, extracting characteristic information from a sequence of air pressure pulsations, and correcting the systolic/diastolic blood pressure on the basis of the characteristic information.

Additional features and advantages of the present disclosure will be set forth in the description which follows, and in part will be apparent from the description, or may be learned by the practice of the present disclosure. The purposes and additional advantages of the present disclosure may be realized and attained by means of the structures particularly pointed out in the description, the claims, and the accompanying drawings.

In order to enable clearer and easier understanding of the above objects, features, and advantages of the present disclosure, preferred embodiments will be described in detail below by way of example with reference to the accompanying drawings.

BRIEF DESCRIPTION OF DRAWINGS

In order to more clearly illustrate technical solutions of specific embodiments of the present disclosure or of the prior art, drawings required for use in the description of the specific embodiments or the prior art will be described briefly below. It is obvious that the drawings in the following description are illustrative of some embodiments of the present disclosure. It will be understood by those of ordinary skill in the art that other drawings can also be obtained from these drawings without any inventive effort.

REFERENCE SIGNS

200—measuring system for electronic sphygmomanometer; 210—acquisition module; 220—calculation module; 230—extraction module; 240—correction module; 300—electronic sphygmomanometer; 310—measuring component.

DETAILED DESCRIPTION OF EMBODIMENTS

In order to further clarify the objects, technical solutions, and advantages of the present disclosure, the technical solutions of the present disclosure will be described below clearly and completely with reference to the accompanying drawings. It is apparent that the embodiments to be described are some, but not all of the embodiments of the present disclosure. All the other embodiments obtained by those of ordinary skill in the art in light of the embodiments of the present disclosure without inventive efforts will fall within the scope of the present disclosure as claimed.

Up to now, air pressure values measured by using an electronic sphygmomanometer, which are either measured during inflation or measured during deflation, are specifically used for calculating an envelope curve, and systolic/diastolic blood pressure of a subject is calculated on the basis of a peak value of the envelope curve. However, the systolic/diastolic blood pressure calculated in this way is calculated using only one parameter which is the envelope curve. The use of a single parameter leads to insufficiently accurate blood pressure calculations. In view of this, the present disclosure provides a measuring method and system for an electronic sphygmomanometer, an electronic sphygmomanometer, and a storage medium, which can increase the accuracy in the calculation of systolic/diastolic blood pressure by calculating the systolic/diastolic blood pressure from a sequence of air pressure values, extracting characteristic information from a sequence of air pressure values, and correcting the systolic/diastolic blood pressure on the basis of the characteristic information.

Figure 1:
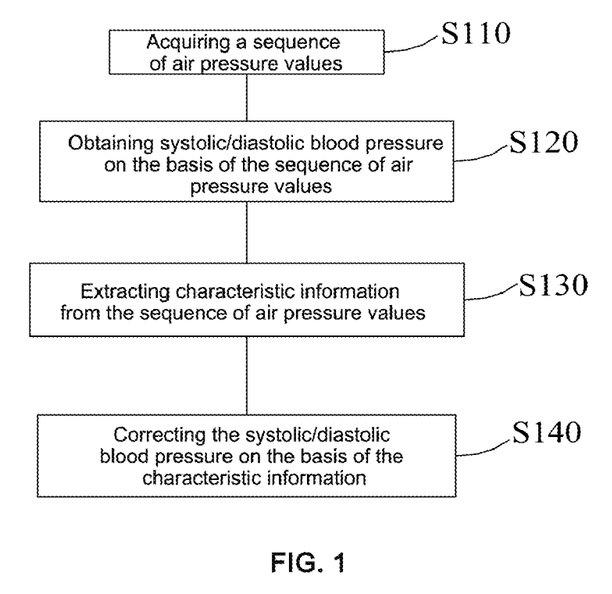
FIG. 1 is a flowchart of a measuring method for an electronic sphygmomanometer according to the present disclosure.

In order to facilitate the understanding of this embodiment, a measuring method for an electronic sphygmomanometer disclosed in the present disclosure will be first described in detail. Referring to FIG. 1, the method comprises following steps.

In step S110, acquiring a sequence of air pressure values.

Specifically, an electronic sphygmomanometer comprises a collecting component and a data processing component. An air bag is taken as an example of the collecting component. When it is necessary to acquire an air pressure value, the air bag may be wrapped around the upper arm or wrist of a human body, and the air bag is inflated/deflated by elements such as an air pump and an air valve connected to the air bag, to collect changes in air pressure value corresponding to the air volume in the air bag. The collected air pressure values are transmitted to the data processing component, so that multiple air pressure values may be acquired. A sequence of air pressure values is formed by the multiple air pressure values. In specific implementation, the multiple air pressure values in the sequence of air pressure values may be arranged sequentially in order of acquisition.

Figure 2:
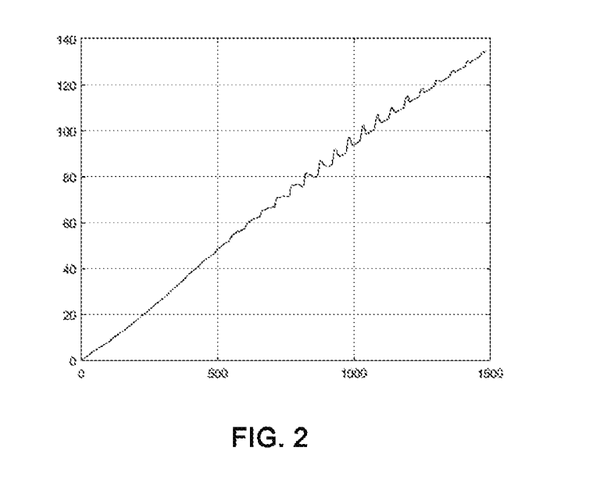
FIG. 2 is a schematic graph showing a value of air pressure in an air bag.

With reference to FIG. 2, the values of air pressure of the air bag are continuously collected during inflation. In FIG. 2, the abscissa represents a sampling point, which is sampled at a frequency of 64 Hz. In other words, 64 samples are collected per second. The 64 points in the abscissa correspond to 1 second. The ordinate represents the air pressure, in unit of mmHg.

In step S120, obtaining systolic/diastolic blood pressure on the basis of the sequence of air pressure values. The systolic/diastolic blood pressure is specifically expressed as systolic blood pressure (SBP) and/or diastolic blood pressure (DBP). The systolic blood pressure may be calculated only, or the diastolic blood pressure may be calculated only, or of course, both the systolic blood pressure and diastolic blood pressure may be calculated.

Figure 3:
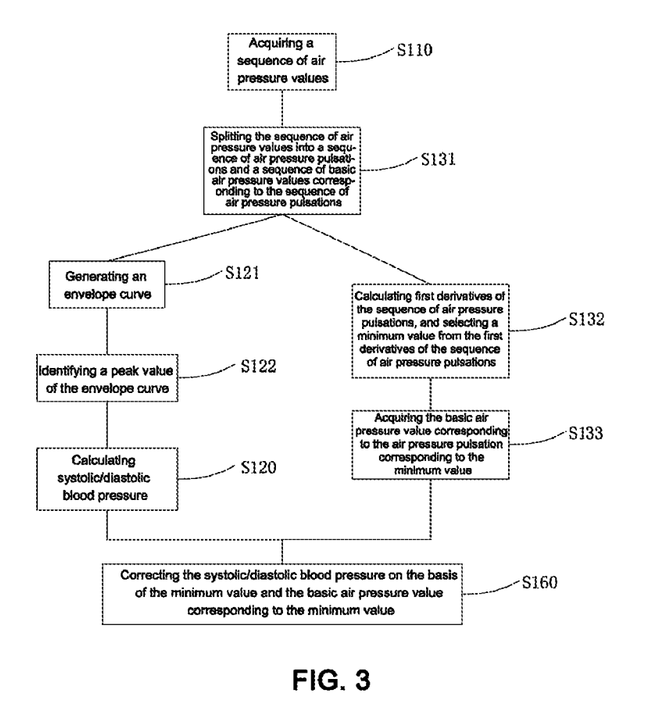
FIG. 3 is a flowchart of a measuring method for an electronic sphygmomanometer according to the present disclosure.

As an example, with reference to FIG. 3, after the step S110 of acquiring a sequence of air pressure values, a step S131 of splitting the sequence of air pressure values into a sequence of air pressure pulsations and a sequence of basic air pressure values corresponding to the sequence of air pressure pulsations may be executed first. Specifically, firstly, a sequence of air pressure pulsations and a sequence of basic air pressure values are separately extracted from the collected sequence of air pressure values. The specific reasons for extracting the sequence of air pressure pulsations and the sequence of basic air pressure values are explained below to facilitate understanding. In the measurement of an air pressure value, the air pressure value is usually affected by two factors to form a graph as shown in FIG. 2. The first factor is a change in air pressure in the air bag, wherein the change in air pressure caused by inflation and deflation is called a change in basic air pressure. The second factor is a change in air pressure in the air bag caused by the pulsation of the blood vessel when the blood vessel in the wrapped part of the human body is compressed by the air bag, wherein the change in air pressure caused by the pulsation of the blood vessel is called air pressure pulsation. When the basic air pressure changes, the degree of compression of the blood vessel by the air bag also changes, and the amplitude of the air pressure pulsation also changes accordingly. In other words, the air pressure value in FIG. 2 specifically refers to a basic air pressure varying continuously and stably on which an air pressure pulsation with a continuously varying oscillation amplitude is superimposed. Hence, a sequence of air pressure pulsations and a sequence of basic air pressure values may be extracted when the sequence of collected air pressure values is post-processed.

Figure 4:
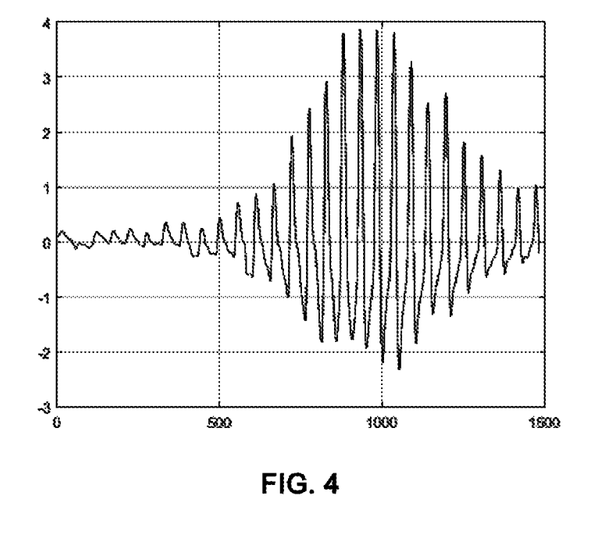
FIG. 4 is a schematic graph showing an air pressure pulsation according to the present disclosure.
Figure 5:
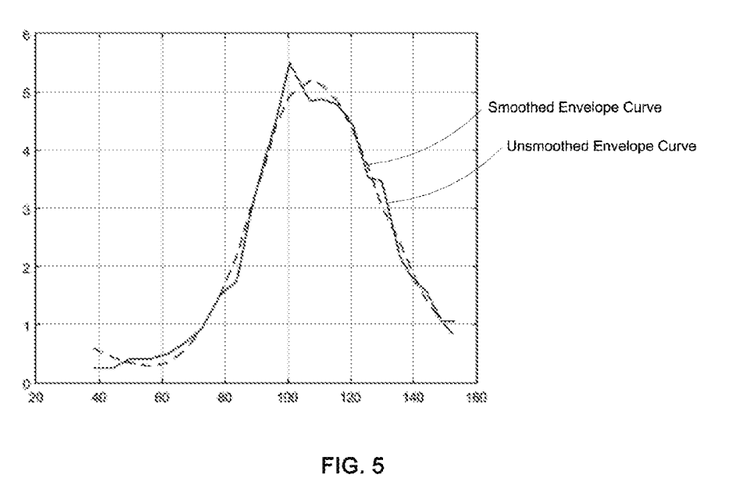
FIG. 5 is a schematic graph showing an envelope curve according to the present disclosure.

In step S121, generating an envelope curve. Specifically, firstly, all the air pressure pulsation values are extracted to obtain an air pressure pulsation graph as shown in FIG. 4. In FIG. 4, the abscissa represents a sampling point, which is sampled at a frequency of 64 Hz. In other words, 64 samples are collected per second. The 64 points in the abscissa correspond to 1 second. The ordinate represents the air pressure, in unit of mmHg. Here, the air pressure pulsation values are extracted from the air pressure values by means of high-pass filtering, or by means of band-pass filtering, moving average filtering, or the like. The amplitudes of all the above-mentioned air pressure pulsation values are taken as ordinates in FIG. 4, and the basic air pressures corresponding to them are taken as abscissas, where both of the abscissa and the ordinate are in unit of mmHg. Considering that the generated initial envelope curve might have sharp points, the envelope curve is smoothed to generate a smoother envelope curve. As shown in FIG. 5, a solid curve represents an unsmoothed envelope curve with multiple sharp points. After the envelope curve is subjected to the smoothing treatment, a dashed curve shown in FIG. 5, i.e., a smoother envelope curve, may be obtained.

As an example, the method for smoothing the envelope curve includes multi-point weighted average, Fourier transform and inverse transform, etc.

Figure 6:
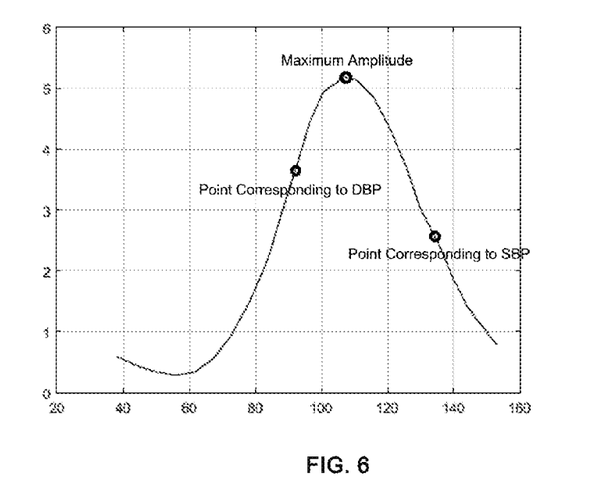
FIG. 6 is a schematic graph showing the position of the systolic/diastolic blood pressure in the envelope curve according to the present disclosure.

In step S122, identifying a peak value of the envelope curve. In other words, the maximum amplitude in the envelope curve is identified. An air pressure pulsation amplitude corresponding to diastolic blood pressure may be obtained after the maximum value of the envelope curve is multiplied by a coefficient for diastolic blood pressure. A point equal to its value may be found on the left side of the envelope curve, and the basic air pressure corresponding to this point is the diastolic blood pressure. An air pressure pulsation amplitude corresponding to systolic blood pressure may be obtained after the aforementioned maximum value of the envelope curve is multiplied by a coefficient for systolic blood pressure. A point equal to its value is found on the right side of the envelope curve, and the basic air pressure corresponding to this point is the systolic blood pressure. With reference to FIG. 6, the maximum amplitude, the point corresponding to diastolic blood pressure (DBP), and the point corresponding to systolic blood pressure (SBP) are shown, respectively. In FIG. 6, the abscissa represents the basic air pressure corresponding to the air pressure pulsation, in unit of mmHg, the ordinate represents the air pressure pulsation amplitude, in unit of mmHg, and the black curve is the smoothed envelope curve.

In addition, both the coefficient for diastolic blood pressure and the coefficient for systolic blood pressure are obtained from analysis of clinical data. In one embodiment, the coefficient for diastolic blood pressure may be in a numerical range of [0.2, 0.7], and the coefficient for systolic blood pressure may be in a numerical range of [0.4, 0.9]. The above numerical ranges are exemplary and illustrative only, and other numerical values may also be used specifically.

It is worth noting that the systolic/diastolic blood pressure calculated above is exemplary only, and other calculation methods are not limited in the present disclosure.

In step S130, extracting characteristic information from the sequence of air pressure values.

The step S130 specifically comprises step S131, step S132, and step S133. The step S131, step S132, and step S133 are further described below with reference to FIGS. 3 and 10.

Figure 10:
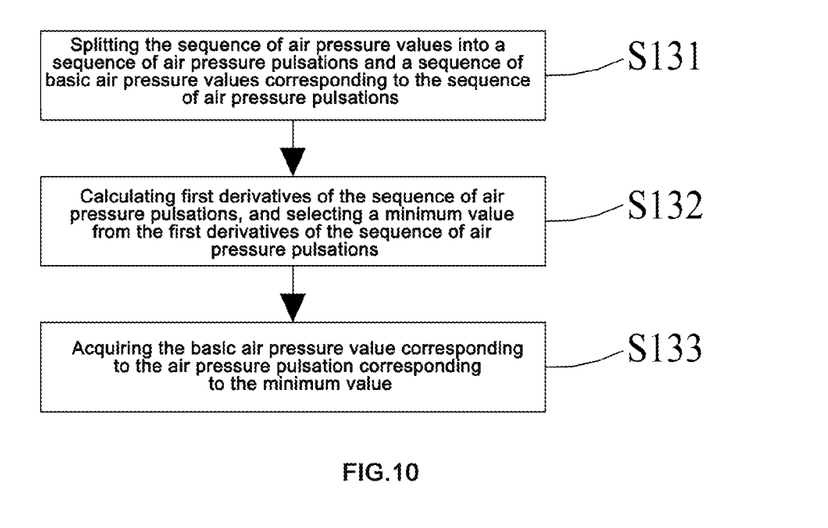
FIG. 10 is a flowchart of extracting characteristic information from a sequence of air pressure values according to the present disclosure.

In step S131, splitting the sequence of air pressure values into a sequence of air pressure pulsations and a sequence of basic air pressure values corresponding to the sequence of air pressure pulsations.

The extracting the sequence of air pressure pulsations from the sequence of air pressure values has been described in the step S120. Details may be understood with reference to the description of the step S120. Specifically, the sequence of basic air pressure values may be extracted from the sequence of air pressure values by means of low-pass filtering, or by means of band-pass filtering, moving average filtering, or the like.

In step S132, calculating first derivatives of the sequence of air pressure pulsations, and selecting a minimum value from the first derivatives of the sequence of air pressure pulsations.

Specifically, the step S132 includes: calculating a difference between the current air pressure pulsation value and the previously measured air pressure pulsation value, and dividing the difference by a sampling period to obtain the first derivative of the current air pressure pulsation; determining the first derivatives of the sequence of air pressure pulsations based on the first derivatives of the respectively measured air pressure pulsation values; and selecting a minimum value from the first derivatives of the sequence of air pressure pulsations as the minimum value of the first derivatives of the sequence of air pressure pulsations.

Figure 7:
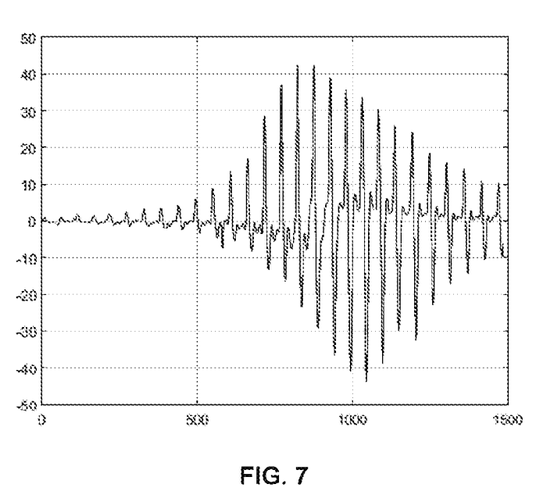
FIG. 7 is a schematic graph showing the first derivative of the air pressure pulsation according to the present disclosure.

Here, the first derivative of the air pressure pulsation may be converted into an air pressure value corresponding to the change in air pressure pulsation per unit time. FIG. 7 shows a schematic graph of the first derivative of the air pressure pulsation. The abscissa represents a sampling point, which is sampled at a frequency of 64 Hz. In other words, 64 samples are collected per second. The ordinate represents the first derivative of the air pressure pulsation, in unit of mmHg/s.

For example, if an air pressure sequence is formed by n air pressure values, n air pressure pulsation values and n basic air pressure values may be separately extracted therefrom. First derivatives for n−1 air pressure pulsations may be calculated by subtracting every two adjacent points of the sequence of air pressure pulsations and dividing each difference by the sampling period. Then, a zero value may be added in front of them to obtain a first derivative sequence of length n. A smallest value is selected as the minimum value, by comparison, from the first derivatives of the n air pressure pulsations.

In step S133, acquiring the basic air pressure value corresponding to the air pressure pulsation corresponding to the minimum value.

For example, a sequence of first derivative values of length n corresponds, in one-to-one manner, to a sequence of basic air pressure values of length n. If the K-th first derivative value is a minimum value, a basic air pressure value corresponding to the K-th first derivative value is the desired basic air pressure value.

In step S140, correcting the systolic/diastolic blood pressure on the basis of the characteristic information.

Specifically, the step S140 includes: correcting the systolic blood pressure according to equation (1), $$Sys = A + B^*Sys0 + C^*Dpmin + D^*Pdpmin \quad (1)$$

where Sys is the corrected systolic blood pressure, Sys0 is the systolic blood pressure to be corrected, Dpmin is the minimum value of the first derivatives of the air pressure pulsations, Pdpmin is the basic air pressure value corresponding to the minimum value, A, B, C, and D are coefficients, A is in unit of mmHg, C is in unit of s, and B and D are dimensionless;

correcting the diastolic blood pressure according to equation (2), $$Dia = E + F^*Dia0 + G^*Dpmin + H^*Pdpmin \quad (2)$$

where Dia is the corrected diastolic blood pressure, Dia0 is the diastolic blood pressure to be corrected, E, F, G, and H are coefficients, E is in unit of mmHg, G is in unit of s, and F and H are dimensionless.

Further, the measuring method further comprises: calculating the values of the coefficients A, B, C, and D in Equation (1) on the basis of systolic blood pressure reference values obtained from multiple clinical data and on the basis of the multiple clinical data; and calculating the values of the coefficients E, F, G, and H in Equation (2) on the basis of diastolic blood pressure reference values obtained from multiple clinical data and on the basis of the multiple clinical data.

The calculating the values of the coefficients A, B, C, and D in Equation (1) on the basis of systolic blood pressure reference values obtained from multiple clinical data and on the basis of the multiple clinical data specifically comprises: acquiring systolic blood pressure reference values from multiple clinical data to form a column vector Y1 of the systolic blood pressure reference values; forming a column vector x1 on the basis of the number of the clinical data; obtaining systolic blood pressure corresponding to each clinical data on the basis of the multiple clinical data to form a column vector x2; obtaining a minimum value of first derivatives of a sequence of air pressure pulsations corresponding to each clinical data on the basis of the multiple clinical data to form a column vector x3; obtaining a basic air pressure value corresponding to the minimum value on the basis of the minimum value of the first derivatives of the sequence of air pressure pulsations corresponding to each clinical data to form a column vector x4; and obtaining the coefficients A, B, C, and D in Equation (1) on the basis of the column vector x1, the column vector x2, the column vector x3, the column vector x4, and the column vector Y1.

Specifically, the values of the coefficients A, B, C, and D in Equation (1) are all obtained from analysis and statistics of effective clinical test data. Clinical data in an amount as large as possible is required as the effective clinical data, and there is such a requirement for the distribution of subjects that the types/blood pressure levels of the subjects are distributed as widely as possible, as shown in Table 1.

TABLE 1

Statistical Table of Distribution Ranges of Subjects

| Item | Distribution Range | | Required Proportion | Required Number | Actual Number | Actual Proportion |
|---|---|---|---|---|---|---|
| Blood Pressure Distribution | Systolic Blood Pressure | ≤100 mmHg | ≥5% | ≥13 groups | 29 | 11.3% |
| | | ≥160 mmHg | ≥5% | ≥13 groups | 14 | 5.5% |
| | | ≥140 mmHg | ≥20% | ≥51 groups | 64 | 25.1% |
| | Diastolic Blood Pressure | ≤60 mmHg | ≥5% | ≥13 groups | 13 | 5.1% |
| | | ≥100 mmHg | ≥5% | ≥13 groups | 14 | 5.5% |
| | | ≥85 mmHg | ≥20% | ≥51 groups | 78 | 30.6% |
| Wrist Circumference Distribution (13.5-21.5 cm) | Upper ¼ of Wrist Circumference Range | | ≥20% | ≥17 persons | 17 | 20.0% |
| | Upper Half of Wrist Circumference Range | | ≥40% | ≥34 persons | 44 | 51.8% |
| | Lower ¼ of Wrist Circumference Range | | ≥20% | ≥17 persons | 17 | 20.0% |
| | Lower Half of Wrist Circumference Range | | ≥40% | ≥34 persons | 41 | 48.2% |
| Gender Distribution | Men | | ≥30% | ≥26 persons | 32 | 37.6% |
| | Women | | ≥30% | ≥26 persons | 53 | 62.4% |
| Age Distribution | Adults (excluding pregnant women) | | | ≥85 persons | 85 | |

Table 1 shows the number and distribution of clinical data used in the present disclosure. The number and distribution range of cases and the testing method for the clinical data may be specifically determined with reference to relevant standards.

Here, the systolic blood pressure reference value obtained from clinical data may be specifically understood as a reference comparison value for systolic blood pressure, which is a systolic blood pressure value that has been obtained from the clinical data.

In some embodiments, obtaining the coefficients A, B, C, and D in Equation (1) on the basis of the column vector x1, the column vector x2, the column vector x3, the column vector x4, and the column vector Y1 includes: fitting P in the equation Y=X*P, preferably, by using the regress function in software Matlab, where P is a column vector of length 4, consisting of elements sequentially corresponding to the coefficients A, B, C, and D in the aforesaid formula for accurate calculation of systolic blood pressure, respectively. The fitting described above may be performed in other ways, for example, by using the polyfit function or the toolbox cftool or the like in the software Matlab, and the trend prediction/regression analysis function of other software such as EXCEL.

The calculating the values of the coefficients E, F, G, and H in Equation (2) on the basis of diastolic blood pressure reference values obtained from multiple clinical data and on the basis of the multiple clinical data specifically comprises: acquiring diastolic blood pressure reference values from multiple clinical data to form a column vector Y2 of the diastolic blood pressure reference values; forming a column vector x5 on the basis of the number of the clinical data; obtaining diastolic blood pressure corresponding to each clinical data on the basis of the multiple clinical data to form a column vector x6; obtaining a minimum value of first derivatives of a sequence of air pressure pulsations corresponding to each clinical data on the basis of the multiple clinical data to form a column vector x7; obtaining a basic air pressure value corresponding to the minimum value on the basis of the minimum value of the first derivatives of the sequence of air pressure pulsations corresponding to each clinical data to form a column vector x8; and obtaining the coefficients E, F, G, and H in Equation (2) on the basis of the column vector x5, the column vector x6, the column vector x7, the column vector x8, and the column vector Y2.

The calculating the values of the coefficients E, F, G, and H in Equation (2) on the basis of diastolic blood pressure reference values obtained from multiple clinical data and on the basis of the multiple clinical data according to an embodiment of the present disclosure is implemented based on the same principle as the embodiment of the calculating the values of the coefficients A, B, C, and D in Equation (1) on the basis of systolic blood pressure reference values obtained from multiple clinical data and on the basis of the multiple clinical data described previously, and may be understood with reference to the corresponding previous description for the sake of a brief description.

The values of A, B, C, D, E, F, G, and H obtained by the above manner may be in respective ranges in one embodiment such that the value of A is in a range of [0, 25], the value of B is in a range of [0, 2], the value of C is in a range of [−0.1, 0.1], the value of D is in a range of [−0.5, 0.5], the value of E is in a range of [0, 25], the value of F is in a range of [0, 2], the value of G is in a range of [−0.1, 0.1], and the value of H is in a range of [−0.5, 0.5]. The above numerical values are exemplary and illustrative only and should not be considered to be limitative.

As an example, 10 adult subjects are randomly selected for comparative measurement. Each subject is tested three times in sequence using an electronic sphygmomanometer (by a known technology), an electronic sphygmomanometer (by the method of the present disclosure), and a mercurial sphygmomanometer, respectively, and their respective mean values are obtained and recorded as shown in Table 2. The result of comparison of test accuracy is shown in Table 3.

TABLE 2

List of Blood Pressure Data Tested by the Method of
the Present Disclosure and by the Known Technology

| Subject No. | Know Technology | | | | Method of the Invention | | | | Reference Value (Mercurial Sphygmomanometer) | |
|---|---|---|---|---|---|---|---|---|---|---|
| | SBP | DBP | SBP Error | DBP Error | SBP | DBP | SBP Error | DBP Error | SBP | DBP |
| 1 | 137 | 85 | 3 | 5 | 139 | 84 | 5 | 4 | 134 | 80 |
| 2 | 105 | 67 | 10 | 4 | 101 | 63 | 6 | 0 | 95 | 63 |
| 3 | 160 | 102 | 5 | −1 | 158 | 105 | 3 | 2 | 155 | 103 |
| 4 | 108 | 67 | −4 | −4 | 106 | 65 | −6 | −6 | 112 | 71 |
| 5 | 111 | 77 | 10 | 6 | 107 | 75 | 6 | 4 | 101 | 71 |
| 6 | 138 | 88 | 4 | −2 | 142 | 92 | 8 | 2 | 134 | 90 |
| 7 | 167 | 96 | −4 | 5 | 169 | 92 | −2 | 1 | 171 | 91 |
| 8 | 113 | 74 | 7 | 5 | 104 | 72 | −2 | 3 | 106 | 69 |
| 9 | 123 | 69 | 9 | −8 | 119 | 70 | 5 | −7 | 114 | 77 |
| 10 | 154 | 75 | −10 | 7 | 158 | 72 | −6 | 4 | 164 | 68 |

As shown in Table 2, there are 10 subjects. Systolic/diastolic blood pressure is calculated using an electronic sphygmomanometer by a known technology and by the method of the present disclosure for the subjects, and systolic/diastolic blood pressure calculated by a mercurial sphygmomanometer is used as the reference comparison value.

TABLE 3

Comparison of Accuracy in Blood Pressure between the Method
of the Present Disclosure and the Known Technology

| | Known Technology | | Method of the Invention | |
|---|---|---|---|---|
| | SBP Error | DBP Error | SBP Error | DBP Error |
| Mean Deviation | 3.00 | 1.70 | 1.70 | 0.70 |
| Standard Deviation | 6.85 | 5.08 | 5.23 | 4.03 |

The mean deviation and standard deviation of systolic/diastolic blood pressure calculated using the known technology and the mean deviation and standard deviation of systolic/diastolic blood pressure calculated using the method of the present disclosure are recorded in Table 3. It can be seen that the systolic/diastolic blood pressure shows a reduction in both mean deviation and standard deviation and is calculated with increased accuracy when the method of the present disclosure is used.

Figure 8:
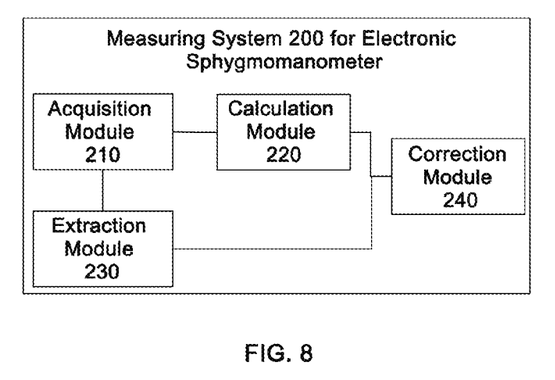
FIG. 8 is a structural view of a measuring system for an electronic sphygmomanometer according to the present disclosure.

Referring to FIG. 8, a measuring system 200 for an electronic sphygmomanometer comprises: an acquisition module 210, a calculation module 220, an extraction module 230, and a correction module 240.

Here, the acquisition module 210 is configured to acquire a sequence of air pressure values. The calculation module 220 is coupled to the acquisition module 210 and configured to obtain systolic/diastolic blood pressure on the basis of the sequence of air pressure values. The extraction module 230 is coupled to the acquisition module 210 and configured to extract characteristic information from the sequence of air pressure values. The correction module 240 is coupled to the calculation module 220 and to the extraction module 230, respectively, and configured to correct the systolic/diastolic blood pressure on the basis of the characteristic information.

In some embodiments, the extraction module 230 specifically comprises: a sequence extraction submodule, configured to separately extract a sequence of air pressure pulsations and a sequence of basic air pressure values from the sequence of air pressure values; a derivative calculation submodule, configured to calculate first derivatives of the sequence of air pressure pulsations and select a minimum value from the first derivatives of the sequence of air pressure pulsations; and an air pressure value acquisition submodule, configured to acquire a basic air pressure value corresponding to an air pressure pulsation corresponding to the minimum value, so as to correct the systolic/diastolic blood pressure by using the minimum value and the basic air pressure value corresponding to the minimum value as characteristic information.

In specific implementation, the sequence extraction submodule is configured to: separately extract a sequence of air pressure pulsations and a sequence of basic air pressure values from the sequence of air pressure values by a high-pass filtering algorithm, a band-pass filtering algorithm, or a moving average filtering algorithm. The derivative calculation submodule is configured to: calculate a difference between the current air pressure pulsation value and the previously measured air pressure pulsation value; divide the difference by a preset sampling period to obtain the first derivative of the current air pressure pulsation value; and determine the first derivatives of the sequence of air pressure pulsations based on the first derivatives of the respectively measured air pressure pulsation values.

In some embodiments, the correction module 240 comprises: a systolic blood pressure correcting submodule, configured to correct the systolic blood pressure according to equation (1), $$Sys = A + B*Sys0 + C*Dpmin + D*Pdpmin \qquad (1)$$

where Sys is the corrected systolic blood pressure, Sys0 is the systolic blood pressure to be corrected, Dpmin is the minimum value of the first derivatives of the air pressure pulsations, Pdpmin is the basic air pressure value corresponding to the minimum value, A, B, C, and D are coefficients, A is in unit of mmHg, C is in unit of s, and B and D are dimensionless; and a diastolic blood pressure correcting submodule, configured to correct the diastolic blood pressure according to equation (2), $$Dia = E + F*Dia0 + G*Dpmin + H*Pdpmin \qquad (2)$$

where Dia is the corrected diastolic blood pressure, Dia0 is the diastolic blood pressure to be corrected, E, F, G, and H are coefficients, E is in unit of mmHg, G is in unit of s, and F and H are dimensionless.

Further, the measuring system for an electronic sphygmomanometer may further comprise: a first calculation module, configured to calculate the values of the coefficients A, B, C, and D in Equation (1) on the basis of systolic blood pressure reference values obtained from multiple clinical data and on the basis of the multiple clinical data; and a second calculation module, configured to calculate the values of the coefficients E, F, G, and H in Equation (2) on the basis of diastolic blood pressure reference values obtained from multiple clinical data and on the basis of the multiple clinical data.

In specific implementation, the first calculation module is configured to: acquire systolic blood pressure reference values from multiple clinical data to form a column vector Y1 of the systolic blood pressure reference values; form a column vector x1 on the basis of the number of the clinical data; obtain systolic blood pressure corresponding to each clinical data on the basis of the multiple clinical data to form a column vector x2; obtain a minimum value of first derivatives of a sequence of air pressure pulsations corresponding to each clinical data on the basis of the multiple clinical data to form a column vector x3; obtain a basic air pressure value corresponding to the minimum value on the basis of the minimum value of the first derivatives of the sequence of air pressure pulsations corresponding to each clinical data to form a column vector x4; and obtain the coefficients A, B, C, and D in Equation (1) on the basis of the column vector x1, the column vector x2, the column vector x3, the column vector x4, and the column vector Y1.

The second calculation module is configured to: acquire diastolic blood pressure reference values from multiple clinical data to form a column vector Y2 of the diastolic blood pressure reference values; form a column vector x5 on the basis of the number of the clinical data; obtain diastolic blood pressure corresponding to each clinical data on the basis of the multiple clinical data to form a column vector x6; obtain a minimum value of first derivatives of a sequence of air pressure pulsations corresponding to each clinical data on the basis of the multiple clinical data to form a column vector x7; obtain a basic air pressure value corresponding to the minimum value on the basis of the minimum value of the first derivatives of the sequence of air pressure pulsations corresponding to each clinical data to form a column vector x8; and obtain the coefficients E, F, G, and H in Equation (2) on the basis of the column vector x5, the column vector x6, the column vector x7, the column vector x8, and the column vector Y2.

The system according to an embodiment of the present disclosure is implemented based on the same principle and achieves the same technical effects as those of the foregoing method embodiments. Parts not mentioned in the device embodiment for the sake of a brief description may be understood with reference to the corresponding description in the foregoing method embodiments.

Figure 9:
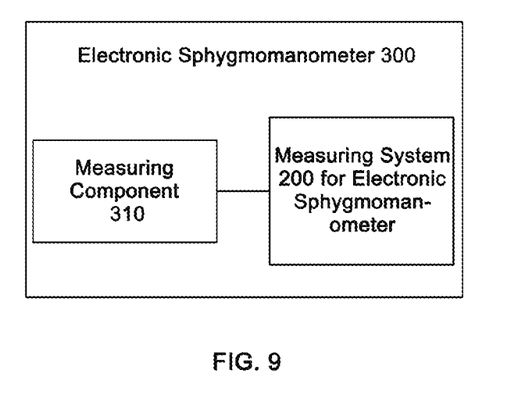
FIG. 9 is a structural view of an electronic sphygmomanometer according to the present disclosure.

Referring to FIG. 9, an electronic sphygmomanometer 300 comprises: a measuring component 310 and the measuring system 200 for an electronic sphygmomanometer according to any one of the above embodiments. Here, the measuring component 310 is configured to apply pressure to a part of a human body to be measured and collect air pressure values.

The measuring system for an electronic sphygmomanometer according to the present disclosure has the same technical features as the measuring system for an electronic sphygmomanometer according to the above embodiment, and therefore can also solve the same technical problems and achieve the same technical effects.

Further, the present disclosure also provides a storage medium, configured to store computer software instructions for use in any one of the measuring methods for an electronic sphygmomanometer described previously.

The relative steps, numerical expressions, and numerical values for the components and steps set forth in these embodiments do not limit the scope of the present disclosure unless it is specifically stated otherwise.

In all examples shown and described herein, any specific value should be construed as illustrative only but not as a limitation, and thus other examples of the exemplary embodiment may have different values.

It should be noted that similar reference signs and letters refer to similar items in the following figures, and thus once a certain item is defined in one figure, it may not be further defined or explained in the following figures.

The flowcharts and block diagrams in the figures illustrate implementable architectures, functionalities, and operations of systems, methods, and computer program products according to multiple embodiments of the present disclosure. In this regard, each block in the flowcharts or block diagrams may represent a module, a program segment, or a portion of code, wherein the module, the program segment, or the portion of code includes one or more executable instructions for implementing specified logical function(s). It should also be noted that in some alternative implementations, the functions shown in the blocks may occur out of the order noted in the figures. For example, two blocks shown in succession may in fact be executed substantially concurrently, or they may sometimes be executed in a reverse order, depending upon the functionality involved. It should also be noted that each block of the block diagrams and/or flowcharts, and combinations of blocks in the block diagrams and/or flowcharts, may be implemented by special purpose hardware-based systems that execute the specified functions or actions, or by a combination of special purpose hardware and computer instructions.

In addition, in the description of the present disclosure, the term "coupled" should be understood broadly unless otherwise expressly specified or defined. For example, connection may be fixed connection or detachable connection or integral connection, may be mechanical connection or electric connection, or may be direct coupling or indirect coupling via an intermediate medium or internal communication between two elements. The specific meanings of the above-mentioned terms in the present disclosure could be understood by those of ordinary skill in the art according to specific situations.

In the description of the present disclosure, it should be noted that orientation or positional relations indicated by the terms such as "up", "down", "left", "right", "inside", and "outside" are the orientation or positional relations shown based on the figures, and these terms are intended only to facilitate the description of the present disclosure and simplify the description, but not intended to indicate or imply that the referred devices or elements must be in a particular orientation, or constructed or operated in the particular orientation, and therefore should not be construed as limiting the present disclosure. In addition, the terms "first", "second", and "third" are used for descriptive purpose only, and should not be understood as an indication or implication of relative importance.

Finally, it should be noted that the embodiments described above are merely specific embodiments of the present disclosure, which are intended to illustrate the technical solutions of the present disclosure and not intended to limit the present disclosure, and to which the scope of protection of the present disclosure is not limited. Although the present disclosure has been described in detail with reference to the foregoing embodiments, it should be understood by those of ordinary skill in the art that the technical solutions described in the foregoing embodiments can be modified, or variations thereof can be readily conceived of, or some of the technical features thereof can be equivalently replaced by those skilled in the art within the technical scope disclosed in the present disclosure; and these modifications, variations, or replacements do not cause the essence of the corresponding technical solution to depart from the spirit and scope of the technical solutions of the embodiments of the present disclosure, and are therefore to be encompassed within the scope of protection of the present disclosure. Therefore, the scope of protection of the present disclosure is to be defined by the scope of protection of the appended claims.

INDUSTRIAL APPLICABILITY

According to the technical solutions of the present disclosure, it is possible for an electronic sphygmomanometer to calculate systolic/diastolic blood pressure more accurately and to further correct the systolic/diastolic blood pressure, which increases well the accuracy in the calculation of the systolic/diastolic blood pressure, so that more accurate and reliable measurement results are obtained by the electronic sphygmomanometer.

What is claimed is:

1. A measuring method for an electronic sphygmomanometer, comprising:
   acquiring a sequence of air pressure values;
   obtaining systolic and diastolic blood pressure according to the sequence of air pressure values;
   extracting characteristic information from the sequence of air pressure values; and
   correcting the systolic and diastolic blood pressure according to the characteristic information;
   wherein the extracting further comprises:
   separately extracting a sequence of air pressure pulsations and a sequence of basic air pressure values from the sequence of air pressure values;
   calculating first derivatives of the sequence of air pressure pulsations, and selecting a minimum value from the first derivatives of the sequence of air pressure pulsations; and
   acquiring a basic air pressure value corresponding to an air pressure pulsation corresponding to the minimum value, so as to correct the systolic and diastolic blood pressure by using the minimum value and the basic air pressure value corresponding to the minimum value as the characteristic information;
   wherein the correcting further comprises:
   correcting the systolic blood pressure according to a first equation, $$Sys=A+B*Sys0+C*Dpmin+D*Pdpmin,$$

where Sys is a corrected systolic blood pressure, Sys0 is a systolic blood pressure to be corrected, Dpmin is the minimum value of the first derivatives of the air pressure pulsations, Pdpmin is the basic air pressure value corresponding to the minimum value, A, B, C, and D are all coefficients, A is in unit of mmHg, and C is in unit of second; and correcting the diastolic blood pressure according to a second equation, $$Dia=E+F*Dia0+G*Dpmin+H*Pdpmin,$$

where Dia is a corrected diastolic blood pressure, Dia0 is a diastolic blood pressure to be corrected, E, F, G, and H are all coefficients, E is in unit of mmHg, and G is in unit of second.

2. The measuring method for an electronic sphygmomanometer according to claim 1, further comprising:
   calculating values of the coefficients A, B, C, and D in the first equation according to systolic blood pressure reference values obtained from multiple clinical data and according to the multiple clinical data; and
   calculating values of the coefficients E, F, G, and H in the second equation according to diastolic blood pressure reference values obtained from multiple clinical data and according to the multiple clinical data.

3. The measuring method for an electronic sphygmomanometer according to claim 2, wherein the calculating values of the coefficients A, B, C, and D in the first equation according to systolic blood pressure reference values obtained from multiple clinical data and according to the multiple clinical data comprises:
   acquiring the systolic blood pressure reference values from the multiple clinical data to form a column vector Y1 of the systolic blood pressure reference values;
   forming a column vector x1 according to the number of the multiple clinical data;
   obtaining systolic blood pressure corresponding to each clinical data according to the multiple clinical data, to form a column vector x2;
   obtaining a minimum value of first derivatives of a sequence of air pressure pulsations corresponding to each clinical data according to the multiple clinical data, to form a column vector x3;
   obtaining a basic air pressure value corresponding to the minimum value according to the minimum value of the first derivatives of the sequence of air pressure pulsations corresponding to each clinical data, to form a column vector x4; and
   obtaining the coefficients A, B, C, and D in the first equation according to the column vector x1, the column vector x2, the column vector x3, the column vector x4, and the column vector Y1.

4. The measuring method for an electronic sphygmomanometer according to claim 2, wherein the calculating values of the coefficients E, F, G, and H in the second equation according to diastolic blood pressure reference values obtained from multiple clinical data and according to the multiple clinical data comprises:
   acquiring the diastolic blood pressure reference values from the multiple clinical data to form a column vector Y2 of the diastolic blood pressure reference values;
   forming a column vector x5 according to the number of the multiple clinical data;
   obtaining diastolic blood pressure corresponding to each clinical data according to the multiple clinical data, to form a column vector x6;
   obtaining a minimum value of first derivatives of a sequence of air pressure pulsations corresponding to each clinical data according to the multiple clinical data, to form a column vector x7;
   obtaining a basic air pressure value corresponding to the minimum value according to the minimum value of the first derivatives of the sequence of air pressure pulsations corresponding to each clinical data to form a column vector x8; and obtaining the coefficients E, F, G, and H in the second equation according to the column vector x5, the column vector x6, the column vector x7, the column vector x8, and the column vector Y2.

5. The measuring method for an electronic sphygmomanometer according to claim 1, wherein the separately extracting a sequence of air pressure pulsations and a sequence of basic air pressure values from the sequence of air pressure values comprises:

separately extracting the sequence of air pressure pulsations and the sequence of basic air pressure values from the sequence of air pressure values using a high-pass filtering algorithm, a band-pass filtering algorithm, or a moving average filtering algorithm.

6. The measuring method for an electronic sphygmomanometer according to claim 1, wherein the calculating first derivatives of the sequence of air pressure pulsations comprises:

calculating a difference between a current air pressure pulsation value and a previously measured air pressure pulsation value; dividing the difference by a preset sampling period to obtain a first derivative of the current air pressure pulsation value;

determining the first derivatives of the sequence of air pressure pulsations based on first derivatives of respectively measured air pressure pulsation values.

7. A measuring system for an electronic sphygmomanometer, comprising a combination of special purpose hardware and computer instructions, wherein, when the computer instructions are run by the special purpose hardware, a plurality of operations are executed, wherein the plurality of operations comprises:

acquiring a sequence of air pressure values;

obtaining systolic and diastolic blood pressure according to the sequence of air pressure values;

extracting characteristic information from the sequence of air pressure values; and correcting the systolic and diastolic blood pressure according to the characteristic information;

separately extracting a sequence of air pressure pulsations and a sequence of basic air pressure values from the sequence of air pressure values;

calculating first derivatives of the sequence of air pressure pulsations and select a minimum value from the first derivatives of the sequence of air pressure pulsations; and acquiring a basic air pressure value corresponding to an air pressure pulsation corresponding to the minimum value, so as to correct the systolic and diastolic blood pressure by using the minimum value and the basic air pressure value corresponding to the minimum value as the characteristic information;

correcting the systolic blood pressure according to a first equation, $$Sys = A + B*Sys0 + C*Dpmin + D*Pdpmin,$$

where Sys is a corrected systolic blood pressure, Sys0 is a systolic blood pressure to be corrected, Dpmin is the minimum value of the first derivatives of the air pressure pulsations, Pdpmin is the basic air pressure value corresponding to the minimum value, A, B, C, and D are all coefficients, A is in unit of mmHg, and C is in unit of second; and correcting the diastolic blood pressure according to a second equation, $$Dia = E + F*Dia0 + G*Dpmin + H*Pdpmin,$$

where Dia is a corrected diastolic blood pressure, Dia0 is a diastolic blood pressure to be corrected, E, F, G, and H are all coefficients, E is in unit of mmHg, and G is in unit of second.

8. The measuring system for an electronic sphygmomanometer according to claim 7, wherein the plurality of operations further comprises:

calculating values of the coefficients A, B, C, and D in the first equation according to systolic blood pressure reference values obtained from multiple clinical data and according to the multiple clinical data; and calculating values of the coefficients E, F, G, and H in the second equation according to diastolic blood pressure reference values obtained from multiple clinical data and according to the multiple clinical data.

9. The measuring system for an electronic sphygmomanometer according to claim 8, wherein the plurality of operations further comprises:

acquiring the systolic blood pressure reference values from the multiple clinical data to form a column vector Y1 of the systolic blood pressure reference values;

forming a column vector x1 according to the number of the multiple clinical data;

obtaining systolic blood pressure corresponding to each clinical data according to the multiple clinical data, to form a column vector x2;

obtaining a minimum value of first derivatives of a sequence of air pressure pulsations corresponding to each clinical data according to the multiple clinical data, to form a column vector x3;

obtaining a basic air pressure value corresponding to the minimum value according to the minimum value of the first derivatives of the sequence of air pressure pulsations corresponding to each clinical data, to form a column vector x4; and obtaining the coefficients A, B, C, and D in the first equation according to the column vector x1, the column vector x2, the column vector x3, the column vector x4, and the column vector Y1.

10. The measuring system for an electronic sphygmomanometer according to claim 8, wherein the plurality of operations further comprises:

acquiring the diastolic blood pressure reference values from the multiple clinical data to form a column vector Y2 of the diastolic blood pressure reference values;

forming a column vector x5 according to the number of the multiple clinical data;

obtaining diastolic blood pressure corresponding to each clinical data according to the multiple clinical data, to form a column vector x6;

obtaining a minimum value of first derivatives of a sequence of air pressure pulsations corresponding to each clinical data according to the multiple clinical data, to form a column vector x7;

obtaining a basic air pressure value corresponding to the minimum value according to the minimum value of the first derivatives of the sequence of air pressure pulsations corresponding to each clinical data, to form a column vector x8; and obtaining the coefficients E, F, G, and H in the second equation according to the column vector x5, the column vector x6, the column vector x7, the column vector x8, and the column vector Y2.

11. The measuring system for an electronic sphygmomanometer according to claim 7, wherein the plurality of operations further comprises: separately extracting the sequence of air pressure pulsations and the sequence of basic air pressure values from the sequence of air pressure values using a high-pass filtering algorithm, a band-pass filtering algorithm, or a moving average filtering algorithm.

12. The measuring system for an electronic sphygmomanometer according to claim 7, wherein the plurality of operations further comprises: calculating a difference between a current air pressure pulsation value and a previously measured air pressure pulsation value; dividing the difference by a preset sampling period to obtain a first derivative of the current air pressure pulsation value; and determining the first derivatives of the sequence of air pressure pulsations based on first derivatives of respectively measured air pressure pulsation values.

13. An electronic sphygmomanometer, comprising: a measuring component and the measuring system for an electronic sphygmomanometer according to claim 7,
wherein the measuring component is configured to apply pressure to a part of a human body to be measured and to collect the sequence of air pressure values.

14. The electronic sphygmomanometer according to claim 13, wherein the plurality of operations further comprises:
separately extracting a sequence of air pressure pulsations and a sequence of basic air pressure values from the sequence of air pressure values;
calculating first derivatives of the sequence of air pressure pulsations and select a minimum value from the first derivatives of the sequence of air pressure pulsations; and
acquiring a basic air pressure value corresponding to an air pressure pulsation corresponding to the minimum value, so as to correct the systolic and diastolic blood pressure by using the minimum value and the basic air pressure value corresponding to the minimum value as the characteristic information;
correcting the systolic blood pressure according to a first equation, $Sys = A + B*Sys0 + C*Dpmin + D*Pdpmin$, where Sys is a corrected systolic blood pressure, Sys0 is a systolic blood pressure to be corrected, Dpmin is the minimum value of the first derivatives of the air pressure pulsations, Pdpmin is the basic air pressure value corresponding to the minimum value, A, B, C, and D are all coefficients, A is in unit of mmHg, and C is in unit of second; and
correcting the diastolic blood pressure according to a second equation, $Dia = E + F*Dia0 + G*Dpmin + H*Pdpmin$, where Dia is a corrected diastolic blood pressure, Dia0 is a diastolic blood pressure to be corrected, E, F, G, and H are all coefficients, E is in unit of mmHg, and G is in unit of second.

15. The electronic sphygmomanometer according to claim 14, wherein the plurality of operations comprises:
calculating values of the coefficients A, B, C, and D in the first equation according to systolic blood pressure reference values obtained from multiple clinical data and according to the multiple clinical data; and
calculating values of the coefficients E, F, G, and H in the second equation according to diastolic blood pressure reference values obtained from multiple clinical data and according to the multiple clinical data.

* * * * *